United States Patent
Chau et al.

(10) Patent No.: US 10,195,411 B2
(45) Date of Patent: Feb. 5, 2019

(54) BLOOD LINE SETS WITH DEFORMABLE BLOOD LINES

(71) Applicant: Fresenius Medical Care Holdings, Inc., Waltham, MA (US)

(72) Inventors: Christopher Yim Chau, Mission, TX (US); Irving Hernandez, Rio Bravo (MX)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 663 days.

(21) Appl. No.: 14/801,622

(22) Filed: Jul. 16, 2015

(65) Prior Publication Data

US 2017/0014613 A1    Jan. 19, 2017

(51) Int. Cl.
*A61M 39/08* (2006.01)
*A61M 1/36* (2006.01)

(52) U.S. Cl.
CPC .......... *A61M 39/08* (2013.01); *A61M 1/3627* (2013.01); *A61M 1/367* (2013.01); *A61M 2209/06* (2013.01)

(58) Field of Classification Search
CPC . A61M 1/3627; A61M 2209/06; A61M 39/08
USPC ................... 604/905, 164.08, 263
See application file for complete search history.

(56) References Cited

U.S. PATENT DOCUMENTS

| | | | |
|---|---|---|---|
| 2,452,643 A * | 11/1948 | Fields | A61M 39/08 285/240 |
| 4,038,983 A | 8/1977 | Mittleman et al. | |
| 4,080,965 A * | 3/1978 | Phillips | A61M 39/14 604/905 |
| 4,586,925 A | 5/1986 | Carlsson et al. | |
| 4,863,429 A * | 9/1989 | Baldwin | A61M 39/08 604/246 |
| 5,119,675 A | 6/1992 | Mohiuddin et al. | |
| 5,163,554 A * | 11/1992 | Lampropoulos | A61M 25/002 206/363 |
| 5,456,676 A * | 10/1995 | Nelson | A61M 39/1055 604/905 |
| 5,830,195 A * | 11/1998 | Peters | A61M 39/1011 604/905 |
| 5,906,598 A | 5/1999 | Giesler et al. | |
| 7,828,774 B2 * | 11/2010 | Harding | A61M 25/0618 604/164.08 |

(Continued)

FOREIGN PATENT DOCUMENTS

| EP | 0244960 A1 * | 11/1987 | ............ A61M 39/08 |
| EP | 2106821 A1 * | 10/2009 | ........ A61M 25/0017 |

(Continued)

*Primary Examiner* — David Bochna

(74) *Attorney, Agent, or Firm* — Fish & Richardson P.C.

(57) ABSTRACT

A tubing set includes a rigid medical fluid chamber, medical fluid tubing, and a cuff. The rigid medical fluid chamber includes a housing and a tubular fitting extending from the housing. The medical fluid tubing is connected to the tubular fitting such that the medical fluid tubing is in fluid communication with the medical fluid chamber. The cuff is positioned over a length of the medical fluid tubing to inhibit denting of a wall of a length of the medical fluid tubing connected to the tubular fitting and extending beyond the tubular fitting. The cuff inhibits denting when the medical fluid tubing is coiled.

31 Claims, 7 Drawing Sheets

(56) References Cited

U.S. PATENT DOCUMENTS

| | | | | |
|---|---|---|---|---|
| 2001/0049519 A1* | 12/2001 | Holman | ............ | A61M 25/0009 |
| | | | | 604/905 |
| 2002/0072712 A1* | 6/2002 | Nool | ................ | A61M 25/0136 |
| | | | | 604/164.08 |
| 2003/0062281 A1* | 4/2003 | Giard, Jr. | ............ | A61M 25/002 |
| | | | | 206/364 |
| 2004/0035743 A1* | 2/2004 | Tighe | ................. | A61M 5/1456 |
| | | | | 206/571 |
| 2004/0078002 A1* | 4/2004 | Rhad | .................. | A61M 5/3273 |
| | | | | 604/164.08 |
| 2005/0015070 A1* | 1/2005 | Delnevo | ............. | A61M 1/1668 |
| | | | | 604/408 |
| 2009/0194453 A1* | 8/2009 | Thorne, Jr. | ............ | A61M 39/16 |
| | | | | 206/571 |
| 2013/0060157 A1* | 3/2013 | Beard | .................. | A61M 16/06 |
| | | | | 600/532 |
| 2013/0112589 A1* | 5/2013 | Lien | ................... | A61M 1/0019 |
| | | | | 206/570 |
| 2014/0091569 A1* | 4/2014 | Spohn | ................. | A61M 39/08 |
| | | | | 285/285.1 |
| 2016/0067435 A1* | 3/2016 | Thomas | ............ | A61M 16/0461 |
| | | | | 128/205.13 |
| 2016/0265698 A1* | 9/2016 | Cai | ....................... | A61M 39/08 |
| 2017/0014613 A1* | 1/2017 | Chau | ..................... | A61M 39/08 |

FOREIGN PATENT DOCUMENTS

| | | | | |
|---|---|---|---|---|
| FR | 2962901 A1 * | 1/2012 | ............ | A61M 39/08 |
| WO | WO-2013016616 A2 * | 1/2013 | ............ | A61M 39/08 |

\* cited by examiner

BLOOD LINE SETS WITH DEFORMABLE BLOOD LINES

TECHNICAL FIELD

This disclosure relates to blood line sets for use in extracorporeal circuits of blood treatment processes.

BACKGROUND

Blood line sets used in extracorporeal blood therapies can include a rigid medical fluid chamber connected to several inlet and/or outlet fluid lines. For convenient storage or packaging, the inlet and outlet fluid lines can be coiled to minimize the space occupied by the blood line set. The fluid lines can also be bent to follow a torturous path from the medical fluid chamber to a destination, such as a patient, a fluid container, a drug vial, or other portion of a fluid circuit.

SUMMARY

Systems and methods pertaining to fluid and blood line sets for medical treatments described herein can include the following features. The blood line set can include a cuff or sleeve that supports a deformable fluid line of the blood line set as the fluid line exits a rigid chamber of the blood line set. As the fluid line bends, the cuff resiliently deforms with the bending fluid line, thus providing additional structural support to the fluid line. The fluid line and the cuff together have a greater rigidity than the fluid line alone. The cuff thus causes a transition in rigidity from the rigid chamber to the fluid line that is more gradual than the fluid line alone.

In one aspect, a tubing set includes a rigid medical fluid chamber, medical fluid tubing, and a cuff. The rigid medical fluid chamber includes a housing and a tubular fitting extending from the housing. The medical fluid tubing is connected to the tubular fitting such that the medical fluid tubing is in fluid communication with the medical fluid chamber. The cuff is positioned over a length of the medical fluid tubing to inhibit denting of a wall of a length of the medical fluid tubing when the medical fluid tubing is coiled. The length of the medical fluid tubing is connected to the tubular fitting and extends beyond the tubular fitting.

In some implementations, the rigid medical fluid chamber has a first rigidity, the medical fluid tubing has a second rigidity less than the first rigidity, and the cuff has a third rigidity greater than the second rigidity and less than the first rigidity. The first rigidity can include a first elastic modulus, the second rigidity can include a second elastic modulus, and the third rigidity can include a third elastic modulus. The first elastic modulus can be between 500 MPa and 2500 MPa, the second elastic modulus can be between 0.5 MPa and 10 MPa, and the third elastic modulus can be between 0.5 and 10 MPa. The first rigidity can include a first wall thickness, the second rigidity can include a second wall thickness, and the third rigidity can include a third wall thickness. The first wall thickness can be between 2 and 5 mm, the second wall thickness can be between 1 mm and 3 mm, and the third wall thickness can be between 2 mm and 4 mm.

In some cases, the rigid medical fluid chamber has a length between 13 cm and 16 cm.

In some examples, the medical fluid tubing can be coiled. The medical fluid tubing can be defined by a radius of curvature. The ratio of the radius of curvature to a length of the rigid medical fluid chamber can be between 0.3 and 0.7. When the medical fluid tubing is coiled, the radius of curvature of the medical fluid tubing can be less than 18 cm. The radius of curvature can be defined by a radius of a 180 degree arc that circumscribes the medical fluid tubing. The arc can include a first end and a second end defining a diameter of the arc. The first end can be located along a free end of the cuff.

In some implementations, the cuff can include first sections having a first outer diameter and second sections having a second outer diameter. The second outer diameter can be less than the first outer diameter. The first and second sections can form a plurality of discontiguous slots. The inner diameter of the cuff can be substantially uniform along a length of the cuff.

In some cases, an inner surface of the cuff can be in contact with an outer surface of the medical fluid tubing and an outer surface of the tubular fitting.

In some examples, an outer surface of the cuff can be in contact with an inner surface of the tubular fitting.

In some implementations, the cuff can be overmolded to the tubular fitting extending from the rigid medical fluid chamber.

In some cases, the cuff can be bonded to the tubular fitting extending from the rigid medical fluid chamber.

In some examples, the cuff can be axisymmetric.

In some implementations, the rigid medical fluid chamber can be an air release chamber having an inlet for blood and an outlet for blood. The outlet can be the tubular fitting of the rigid medical fluid chamber.

In another aspect, a package of medical fluid tubing sets includes a compartment, at least one medical fluid tubing set, and a cuff. The compartment has a compartment length. The at least one medical fluid tubing set includes a rigid medical fluid chamber, medical fluid tubing, and a cuff. The rigid medical chamber has a chamber length and includes a housing and a tubular fitting extending from the housing. The medical fluid tubing is connected to the tubular fitting such that the medical fluid tubing is in fluid communication with the medical fluid chamber. The cuff is positioned over a length of the medical fluid tubing to inhibit denting of a wall of a length of the medical fluid tubing when the medical fluid tubing is coiled. The length of the medical fluid tubing is connected to the tubular fitting and extends beyond the tubular fitting. A ratio of the chamber length to the compartment length is greater than 0.7.

In some implementations, the rigid medical fluid chamber can have a length between 13 cm and 16 cm.

In some cases, the medical fluid tubing can be coiled and defined by a radius of curvature. A ratio of the radius of curvature to a length of the rigid medical fluid chamber can be between 0.3 and 0.7. When the medical fluid tubing is coiled, the radius of curvature of the medical fluid tubing can be less than 18 cm. The radius of curvature can be defined by a radius of a 180 degree arc that circumscribes the medical fluid tubing. The arc can include a first end and a second end defining a diameter of the arc. The first end can be located along a free end of the cuff.

In some examples, the radius of curvature of the medical fluid tubing can be less than 18 cm. The radius of curvature can be defined by a radius of a 180 degree arc that circumscribes the medical fluid tubing. The arc can include a first end and a second end defining a diameter of the arc. The first end can be located along a free end of the cuff.

In some implementations, the rigid medical fluid chamber has a first rigidity, the medical fluid tubing has a second rigidity less than the first rigidity, and the cuff has a third rigidity greater than the second rigidity and less than the first rigidity. The first rigidity can include a first elastic modulus, the second rigidity can include a second elastic modulus, and the third rigidity can include a third elastic modulus. The first elastic modulus can be between 500 MPa and 2500 MPa, the second elastic modulus can be between 0.5 MPa and 10 MPa, and the third elastic modulus can be between 0.5 and 10 MPa. The first rigidity can include a first wall thickness, the second rigidity can include a second wall thickness, and the third rigidity can include a third wall thickness. The first wall thickness can be between 2 and 5 mm, the second wall thickness can be between 1 mm and 3 mm, and the third wall thickness can be between 2 mm and 4 mm.

In some cases, the rigid medical fluid chamber has a length between 13 cm and 16 cm.

In some implementations, the cuff can include first sections having a first outer diameter and second sections having a second outer diameter. The second outer diameter can be less than the first outer diameter. The first and second sections can form a plurality of discontiguous slots. The inner diameter of the cuff can be substantially uniform along a length of the cuff.

In some cases, an inner surface of the cuff can be in contact with an outer surface of the medical fluid tubing and an outer surface of the tubular fitting.

In some examples, an outer surface of the cuff can be in contact with an inner surface of the tubular fitting.

In some implementations, the cuff can be overmolded to the tubular fitting extending from the rigid medical fluid chamber.

In some cases, the cuff can be bonded to the tubular fitting extending from the rigid medical fluid chamber.

In some examples, the cuff can be axisymmetric.

In some implementations, the rigid medical fluid chamber can be an air release chamber having an inlet for blood and an outlet for blood. The outlet can be the tubular fitting of the rigid medical fluid chamber.

Certain implementations can include the one or more of the following advantages. The cuff can structurally support the fluid line of the blood line set such that the fluid line can bend without causing material damage to the fluid lines. As a result, a user can more easily and safely guide and bend the fluid lines so that the fluid lines can reach target destinations of the fluid, such as, for example, a patient, a saline bag, a drug vial, or other waypoint for fluids in a therapy process. The cuff further allows the fluid line of the blood line set to be coiled so that the user can more compactly package the blood line set without causing material damage to the fluid line. The fluid line with the cuff can be coiled into a loop having a smaller average radius of curvature as compared to a fluid line without the cuff. Boxes, pouches, cartons, and other packaging products for the blood line sets can therefore be smaller and/or fit additional blood line sets.

Other aspects, features, and advantages will be apparent from the description and drawings, and from the claims.

DETAILED DESCRIPTION

During a medical treatment of blood, such as hemodialysis, blood can circulate through an extracorporeal circuit, which can include a blood line set. The blood line set can include a length of medical fluid tubing connected to a rigid medical fluid chamber, such as a drip chamber or an air release chamber. Before treatment, the blood line set is typically stored in sterile packaging (e.g., a pouch, a container, a box, etc.). The medical fluid tubing is flexible and thus can be coiled so that the blood line set can be easily stored without unnecessarily occupying space. The tubing of the blood line set can also bend to follow a curved path between the medical fluid chamber and, e.g., a patient, a saline container, or a drug container. The medical fluid lines are connected to and in fluid communication with the rigid medical fluid chamber. A transition from a flexible section (e.g., the medical fluid tubing) to a rigid section (e.g., the medical fluid chamber) can result in bending that includes, for example, a stress concentration or an interruption in gradual or uniform bending characteristics. Portions of the fluid lines along the transition can experience higher levels of stress than other portion of the fluid lines, thus increasing a risk of inelastic deformation occurring in walls of the fluid lines along the transition. A cuff of the type described herein can alleviate the stresses present at these interface locations to reduce the risk of inelastic deformation of the medical fluid tubing.

Figure 1:
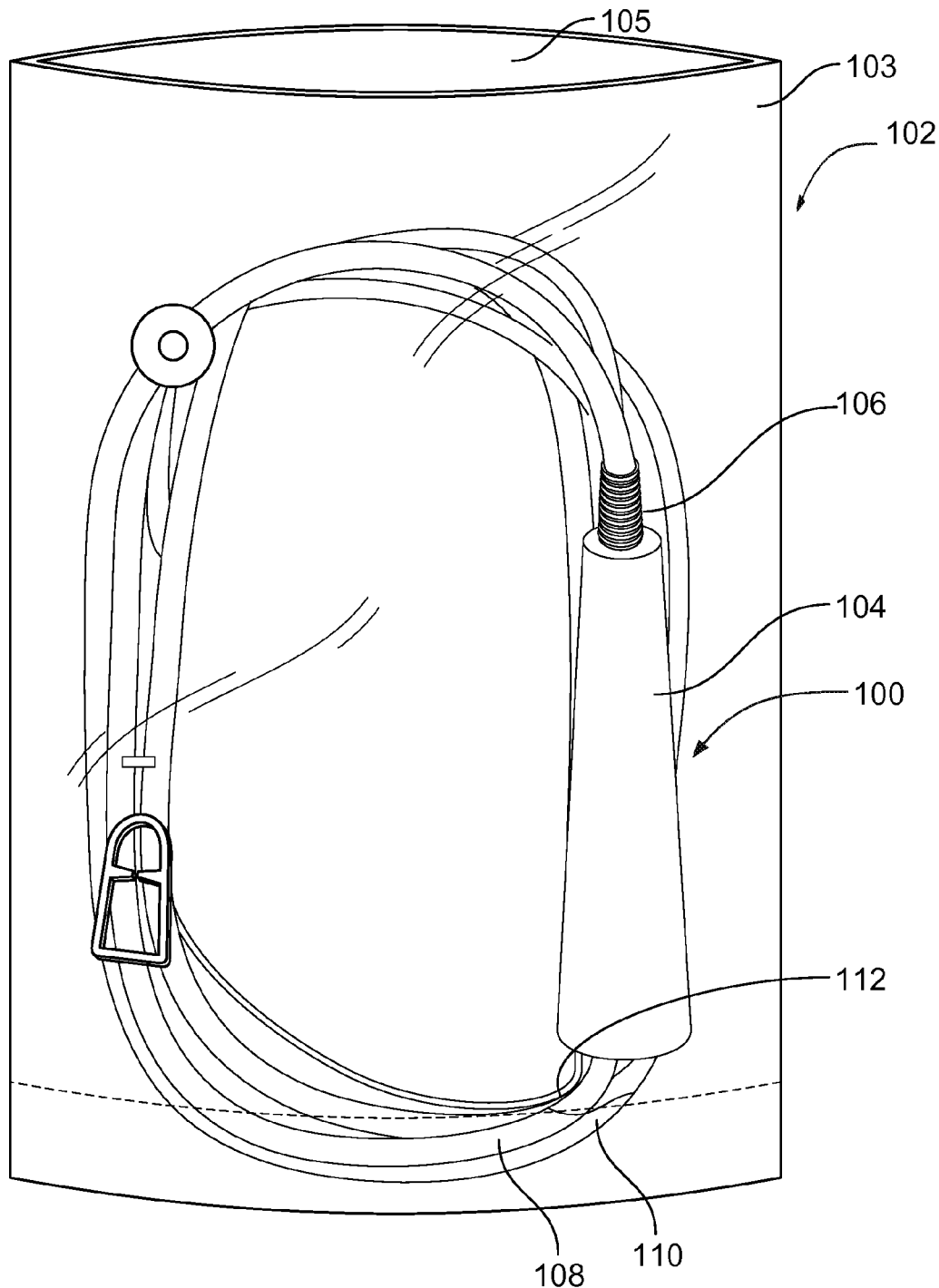
FIG. 1 is a front perspective view of an example of a blood line set coiled in a pouch.

As shown in FIG. 1, a blood line set 100 is compactly and sterilely packaged within a pouch 102. The pouch 102 is a sterile medical device container that is flexible and can be formed of a paper backing with a polymer film 105 fixed to a paper backing 103. The blood line set 100 can be placed and sealed inside a compartment of the pouch 102 formed between the paper backing 103 and the polymer film 105 of the pouch 102 to separate the blood line set 100 from the environment. The pouch 102 can be peelable so that the pouch 102 can be opened and the blood line set 100 can be easily removed from the pouch 102. The blood line set 100 includes a rigid medical fluid chamber 104, an outlet fluid line 106, a first inlet fluid line 108, a second inlet fluid line 110, and a third inlet fluid line 112. The fluid lines 106, 108, 110, and 112 are medical fluid tubing that can be extruded from polymeric resin. Each of the fluid lines 106, 108, 110, and 112, as shown, is coiled to fit within the pouch 102.

The pouch 102 is sized and dimensioned to receive the medical fluid chamber 104 when the fluid lines 106, 108, 110, 112 are coiled about the rigid medical fluid chamber 104. To accommodate the medical fluid chamber 104 and the coiled fluid lines 106, 108, 110, 112, the pouch 102 has a length that accommodates the length of the medical fluid chamber 104 and an average radius of curvature of the coiled fluid lines 106, 108, 110, 112. The blood line set 100 also includes a cuff 122 that reduces the average radius of curvature of the coiled fluid lines 106, 108, 110, 112 that can be achieved without damaging the walls of the fluid lines 106, 108, 110, 112. The cuff 122 thus decreases the size of the compartment of the pouch 102 and the size of the pouch 102 needed to accommodate the blood line set 100. The average radius of curvature of the fluid lines 106, 108, 110, 112 that can be achieved from bending or coiled the fluid lines 106, 108, 110, 112 will be described in more detail below.

The medical fluid chamber 104 can have a length between 10 and 21 cm. The length and width of the pouch 102 can be 15 cm to 30 cm. The projected area of the pouch 102 (e.g., the product of the length and the width of the pouch 102) can be 225 square centimeters to 900 square centimeters. The ratio of the length of the medical fluid chamber 104 to the length and/or width of the pouch 102 can be greater than 0.7.

Figure 2:
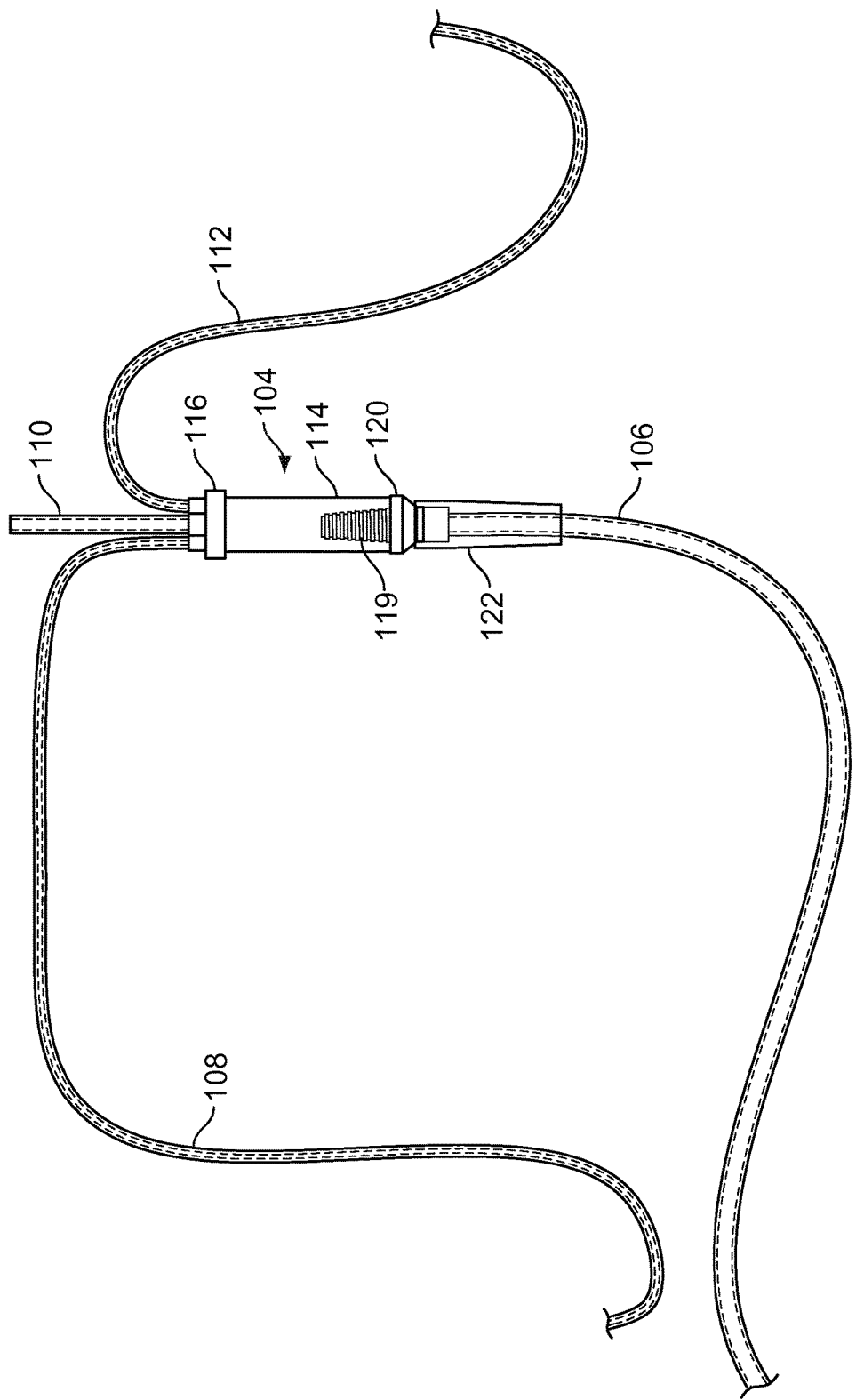
FIG. 2 is a schematic front view of a medical fluid chamber and a venous blood line portion of the blood line set of FIG. 1.

When the blood line set 100 is removed from the pouch 102, the blood line set 100 is uncoiled, as shown in FIG. 2. The inlet fluid lines 108, 110, 112 enter into a housing 114 of the medical fluid chamber 104 through a cap 116 of the medical fluid chamber 104. The outlet fluid line 106 exits the medical fluid chamber 104 through a tubular fitting 120 of the medical fluid chamber 104. The tubular fitting 120 extends from the housing 114 and serves as a fluid outlet for the medical fluid chamber 104. Both the inlet fluid lines 108, 110, 112 and the outlet fluid line 106 can follow tortuous or curved paths that result in bending stresses throughout walls of the fluid lines 106, 108, 110, 112.

A filter 119 disposed in the medical fluid chamber 104 and above the tubular fitting 120 removes particulate matter and debris (e.g., clots) entrained in fluid entering the medical fluid chamber 104 through the inlet fluid lines 108, 110, 112. During use, fluid enters the medical fluid chamber 104 through the inlet fluid lines 108, 110, 112 and exits the medical fluid chamber 104 through the outlet fluid line 106, passing through the filter 119 to remove particulate matter from the fluid.

The outlet fluid line 106 is connected to the tubular fitting 120 such that the outlet fluid line 106 is in fluid communication with the medical fluid chamber 104. To equalize the flow rate out of the medical fluid chamber 104 and the flow rate into the medical fluid chamber 104, the outlet fluid line 106 permits a greater flow rate than each of the flow rates through the inlet fluid lines 108, 110, 112. The combined flow rates through the inlet fluid lines 108, 110, 112 can be approximately equal to the flow rate through the outlet fluid line 106 so that the medical fluid chamber 104 does not overflow with fluid during use. The outlet fluid line 106 has a greater inner diameter than the inlet fluid lines 108, 110, 112 to achieve the equalized flow rates.

Figure 3:
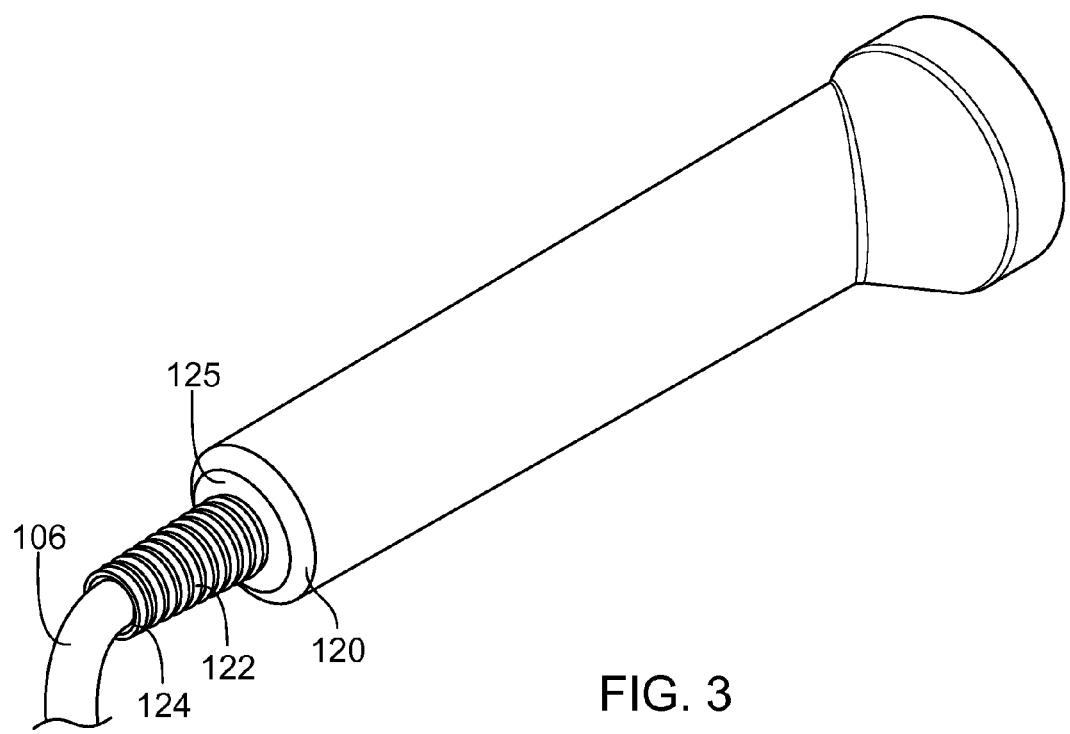
FIG. 3 is an enlarged perspective view of the medical fluid chamber of the blood line set of FIG. 2.

Referring to both FIGS. 2 and 3, the cuff 122 is positioned over a portion or a length of the outlet fluid line 106 that is connected to the tubular fitting 120. The portion of the outlet fluid line 106 with the cuff 122 extends beyond the tubular fitting 120. The cuff 122 also is positioned over a portion of the tubular fitting 120. The cuff 122 defines an opening 124 so that the cuff 122 can fit around both the tubular fitting 120 of the medical fluid chamber 104 and the outlet fluid line 106. An inner diameter of the opening 124 of the cuff 122 is approximately equal to an outer diameter of the tubular fitting 120 so that the cuff fits over the tubular fitting 120. As shown in FIG. 3, the cuff 122 abuts a bottom surface 125 of the housing 114 of the medical fluid chamber 104. An inner surface of the cuff 122 is in contact with or engages an outer surface of the outlet fluid line 106. The inner surface of the cuff 122 is also engaged with an outer surface of the tubular fitting 120.

The cuff 122 and the medical fluid chamber 104 can be formed using, for example, an injection molding process. The cuff 122, for example, can be overmolded or insert molded on the medical fluid chamber 104. The outlet fluid line 106 can be formed using, for example, an extrusion process.

Figure 4:
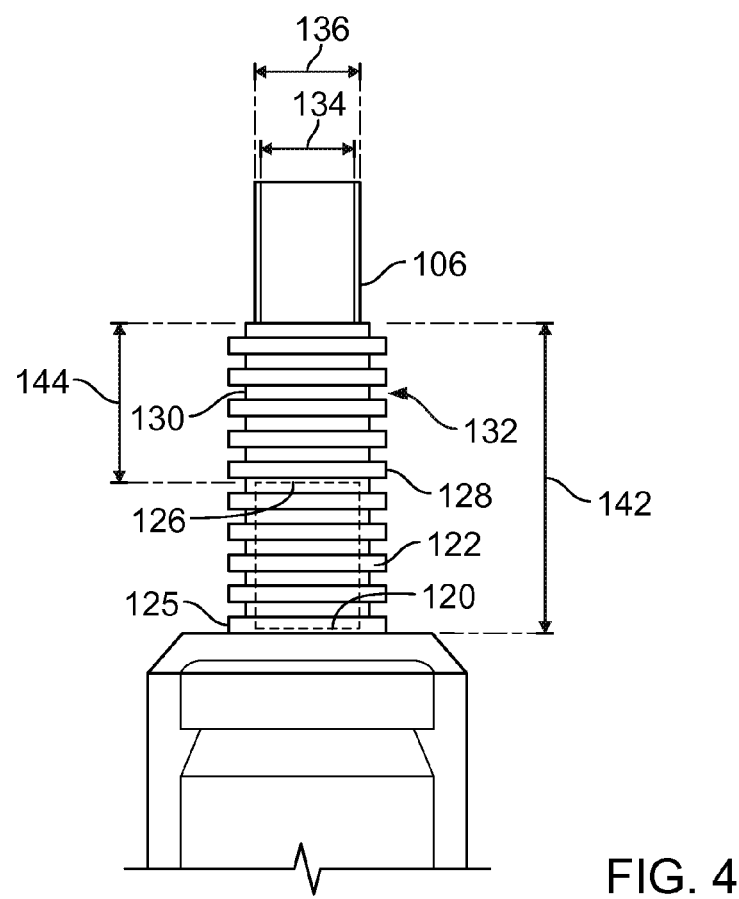
FIG. 4 is a front view of a cuff attached to the medical fluid chamber of the blood line set of FIG. 2.

FIG. 4 shows a front view of the cuff 122 disposed over the tubular fitting 120 of the medical fluid chamber 104. The cuff 122 extends in a downward direction from the bottom surface 125 of the housing 114 toward an end 126 of the tubular fitting 120. The cuff 122 includes multiple discontiguous protruding sections 128 connected by multiple discontiguous recessed sections 130. The protruding sections 128 and the recessed sections 130 define circular slots 132. The cuff 122 can be axisymmetric about a longitudinal axis of the cuff 122.

The medical fluid chamber 104, the fluid lines 106, 108, 110, 112, and the cuff 122 have geometric properties (e.g., a wall thickness, moment of inertia) and material properties (e.g., elastic modulus, yield strength) that make the medical fluid chamber 104 more rigid (e.g., have a greater flexural rigidity) than the fluid lines 106, 108, 110, 112 and the cuff 122. With respect to geometric properties, the outlet fluid line 106 can have an inner diameter between 3 and 5 mm, an outer diameter between 5 and 7 mm, and a wall thickness between 1 and 3 mm. The medical fluid chamber 104 can have a wall thickness between 2 and 4 mm. The cuff 122 can have an inner diameter to accommodate the outlet fluid line 106. At the protruding sections 128 of the cuff 122, the cuff 122 can have a wall thickness of between 2 mm and 4 mm. At the recessed sections 130 of the cuff 122, the cuff 122 can have a wall thickness between 1 mm and 3 mm. The protruding sections 128 can be spaced apart between 0.5 mm and 2 mm. The recessed sections 128 can be spaced by 0.5 mm to 2 mm. The cuff 122 can have a total length 142 of 2 cm to 6 cm. A length 144 included in the total length 142 extends beyond the tubular fitting 120 (e.g., by 1 cm to 3 cm). Together, the cuff 122 and the outlet fluid line 106 can have a combined minimum wall thickness (e.g., at the recessed sections 130) of 2 mm to 6 mm and a combined maximum wall thickness (e.g., at the protruding sections 128) of 3 mm to 7 mm.

The cuff 122 is generally formed of a resilient polymer, such as an elastomer or rubber (e.g., latex, silicone, ethylene propylene rubber, ethylene propylene diene rubber, silicone rubber, fluoroelastomers, polyether block amides, or a blended polymer including a rubber). The medical fluid chamber 104 and the medical fluid lines 106, 108, 110, and 112 are generally formed of a polymer such as polyvinyl chloride (PVC), polycarbonate (PC), acrylonitrile butadiene styrene (ABS), or nylon. The material of the cuff 122 can have an elastic modulus between 0.5 MPa to 10 MPa. The material of the outlet fluid line 106 can have an elastic modulus between 0.5 MPa to 10 MPa. The material of the medical fluid chamber 104 can have an elastic modulus between, for example, 500 MPa to 2500 MPa. The medical fluid chamber 104 can have a durometer of shore 70D to 85D. The medical fluid lines 106, 108, 110, 112 can have a durometer of shore 70 A to 85 A. The cuff 122 can have a durometer of shore 70 A to 85 A.

Bending of the fluid lines 106, 108, 110, 112 results in stresses within the walls of the fluid lines 106, 108, 110, 112 that increase with increased bending. As described herein, the inner diameter of the outlet fluid line 106 is greater than the inner diameter of the inlet fluid lines 108, 110, 112. As a result, for an amount of bending of the fluid lines 106, 108, 110, 112, the walls of the outlet fluid line 106 experience greater stresses than the walls of the inlet fluid lines 108, 110, 112. Thus, the outlet fluid line 106 is more susceptible to material failure modes such as kinking (e.g., wall-to-wall collapse of the outlet fluid line 106) and denting (e.g., inelastic deformation of wall of the outlet fluid line 106) when the outlet fluid line 106 is bent Kinking and denting occur due to yielding (e.g., inelastic deformation) or localized buckling of the outlet fluid line 106. Generally, the likelihood of these failure modes occurring for the outlet fluid line 106 depend on the material properties and the geometric properties of the outlet fluid line 106 and other components supporting the outlet fluid line 106. Additionally, greater stresses and forces cause the failure modes to occur.

For localized buckling, a support condition of the outlet fluid line 106 influences the likelihood of localized buckling by modifying the stress conditions on the outlet fluid line 106. The outlet fluid line 106 is connected to, and thus supported by, the medical fluid chamber 104 so that the outlet fluid line 106 is in fluid communication with the medical fluid chamber 104. The outlet fluid line 106 is less rigid than the medical fluid chamber 104 so that the outlet fluid line 106 can follow a tortuous or curved path to target destinations. The outlet fluid line 106 and the medical fluid chamber 104 thus have large differences in rigidity, and the connection between the outlet fluid line 106 and the medical fluid chamber 104 can be considered a fixed support condition for the outlet fluid line 106. Thus, the outlet fluid line 106 is susceptible to kinking, yielding, and localized buckling where the outlet fluid line 106 is abruptly fixed to the tubular fitting 120 of the medical fluid chamber 104.

The cuff 122 inhibits the above-described failure modes from occurring by supporting the outlet fluid line 106. When the cuff 122 is positioned over the outlet fluid line 106, the properties of the cuff 122 are combined with the properties of the outlet fluid line 106 such that their combined properties (e.g., an average elastic modulus and a combined moment of inertia) inhibit kinking, denting, buckling, yielding, and other failure modes of the material of the outlet fluid line 106. The cuff 122 and the outlet fluid line 106 together have a greater combined wall thickness than the outlet fluid line 106 alone. Thus, the cuff 122 and the outlet fluid line 106 have a greater combined moment of inertia such that stresses are distributed through the walls of both the cuff 122 and the outlet fluid line 106.

The difference in flexural rigidity (i.e., a product of an elastic modulus and a moment of inertia) between the combination of the cuff 122 and outlet fluid line 106 and the medical fluid chamber 104 is less than the difference in flexural rigidity of the outlet fluid line 106 alone and the medical fluid chamber 104. The cuff 122 thus functions to change the support condition of the outlet fluid line 106 by flexibly and gradually fixing the outlet fluid line 106 to the tubular fitting 120. The gradual fixed condition increases the minimum required loads to buckle the outlet fluid line 106 relative to the abrupt fixed condition where the outlet fluid line 106 is connected to the medical fluid chamber 104 without the cuff 122. Thus, the cuff 122 advantageously reduces kinking and denting, among other failure modes, of the outlet fluid line 106 when the outlet fluid line 106 is bent, coiled, or curved.

Figure 5:
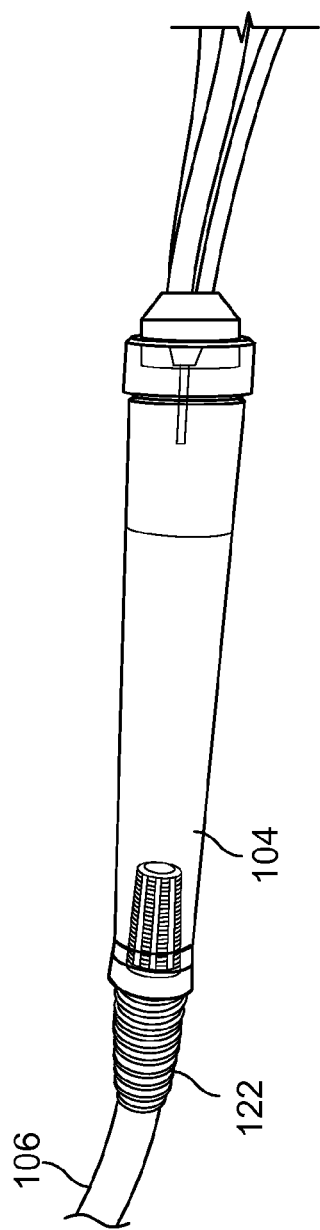
FIG. 5 is a front view of the blood line set of FIG. 2 in a straight configuration.
Figure 6:
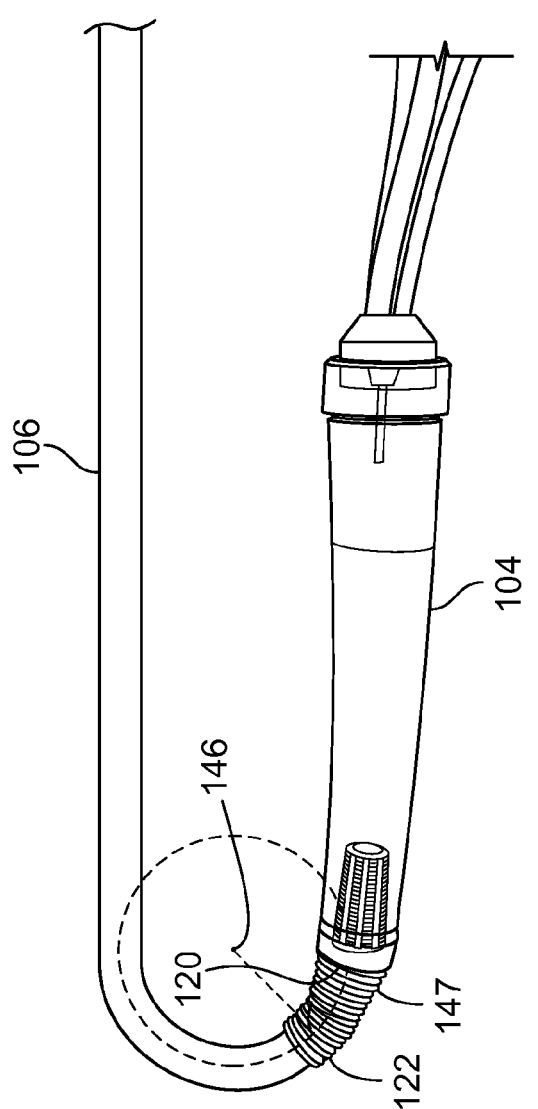
FIG. 6 is a front view of the blood line set of FIG. 2 in a curved configuration.

FIGS. 5 and 6 show the outlet fluid line 106 in a straight and curved configuration, respectively. When the outlet fluid line 106 is in the straight configuration, as shown in FIG. 5, the outlet fluid line 106 does not experience significant deformation. The walls of outlet fluid line 106 thus do not experience significant stresses that can cause material failure of the walls.

During normal use and/or transport, the medical fluid chamber 104 does not substantially deform (e.g., deform more than 1 to 5 mm) from forces exerted on the medical fluid chamber 104. The cuff 122 and the outlet fluid line 106, however, visibly deform and bend. The bending of the cuff 122 and the outlet fluid line 106 are defined by average radii of curvature. When the outlet fluid line 106 is in the curved configuration, as depicted in FIG. 6, the deformation of the outlet fluid line 106 causes bending stresses in the walls of the outlet fluid line 106, which in turn leads to, for example, buckling, yielding, kinking, denting, and/or other material failures. An average radius of curvature 146 as the outlet fluid line 106 exits the medical fluid chamber 104 defines an average amount of bending deformation of the outlet fluid line 106 in the curved configuration. The average radius of curvature is geometrically defined by a radius of a 180 degree arc that follows a path of or circumscribes the outlet fluid line 106. The arc includes a first end located at an end of the cuff 122 as the outlet fluid line 106 exits the cuff 122 and a second end that, with the first end, defines a diameter of the arc. With the cuff 122, the minimum average radius of curvature 146 without causing material damage of the outlet fluid line 106 is typically less than 10 cm. When the outlet fluid line 106 is coiled, a ratio of the average radius of curvature 146 to the length of the medical fluid chamber 104 can be between 0.3 and 0.7.

The localized bending of the outlet fluid line 106 near the medical fluid chamber 104 is defined by a localized radius of curvature that is greater than the average radius of curvature 146. The localized bending causes higher stresses in the walls of the outlet fluid line 106. For example, in a case where the cuff 122 does not support the outlet fluid line 106 as the outlet fluid line 106 exits the medical drip chamber 104, the outlet fluid line 106 experiences localized bending when the outlet fluid line 106 bends against a high rigidity surface, such as an edge 147 of the tubular fitting 120 that has a much higher overall rigidity than the outlet fluid line 106. Even though the outlet fluid line 106 may have an average radius of curvature 146 below an amount that can cause material failure of the outlet fluid line 106, the localized bending and the localized radius of curvature at the interface between the outlet fluid line 106 and the edge 147 can be less than the average radius of curvature. The outlet fluid line 106 thus becomes susceptible to the failure modes described herein due to the higher stresses caused by the smaller localized radius of curvature.

The cuff 122 reduces the occurrence of such localized bending. As the outlet fluid line 106 exits the tubular fitting 120, the cuff 122 prevents the outlet fluid line 106 from severely bending against the edge 147 of the tubular fitting 120. The cuff 122 and the outlet fluid line 106 together are more rigid (e.g., have a higher moment of inertia and/or a higher moduli of elasticity) than the outlet fluid line 106 alone and thus tend to limit the localized bending around the tubular fitting 120. Because the cuff 122 is less stiff than the tubular fitting 120, localized bending of the outlet fluid line 106 that may occur—for example, as the outlet fluid line 106 exits the cuff 122 and bends against the cuff 122—tends to cause radii of curvature that are greater than the radii of curvature expected from the outlet fluid line 106 directly bending against the tubular fitting 120.

The smallest average radius of curvature 146 that would not cause material failure of the outlet fluid line 106 is smaller when the outlet fluid line 106 is supported by the cuff 122 than when the outlet fluid line 106 is not supported by the cuff 122. The cuff 122 thus allows the blood line set 100 to be more compactly packaged without risk of damaging the outlet fluid line 106. In particular, the outlet fluid line 106 can be more tightly coiled into coils having the average radius of curvature 146 described herein.

Figure 7:
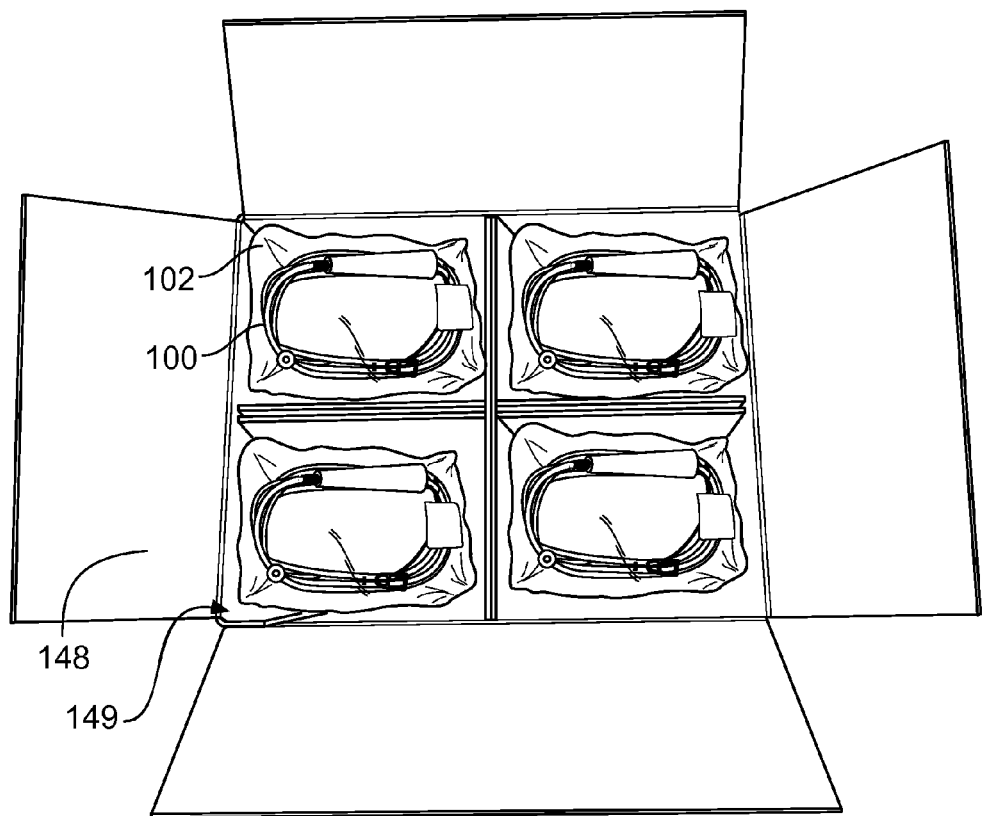
FIG. 7 is a top view of a carton containing multiple pouches and blood line sets of the type shown in FIG. 1.

Referring to FIG. 7, blood line sets 100 are packaged in pouches 102 and placed in a carton 148. Also referring to FIG. 8, the outlet fluid lines 106 and the inlet fluid lines 108, 110, 112 (shown in FIG. 1) of each blood line set 100 are tightly coiled. The outlet fluid lines 106 are coiled to achieve, as described herein, the minimum average radius of curvature 146 without causing material failure of the walls of the outlet fluid line 106. Since the inlet fluid lines 108, 110, 112 have smaller inner and outer diameters than the inner and outer diameters of outlet fluid lines 106, the inlet fluid lines 108, 110, 112 experience less stresses than the outlet fluid lines 106 for a given average radius of curvature. The inlet fluid lines 108, 110, 112 thus generally can be coiled to an average radius of curvature of a similar size to the average radius of curvature of the outlet fluid lines 106 without risk of material failure. The average radius of curvature of the outlet fluid line 106 thus limit the size of the coils of the fluid lines 106, 108, 110, 112. The size of the pouch 102 can thus be minimized to fit the compactly packed blood line sets 100 by coiling the fluid lines 106, 108, 110, 112 to have the average radius of curvature 146 described above.

The carton 148 includes four compartments 149 that each accommodate multiple pouches 102 containing the blood line sets 100. The pouches 102 can be stacked on top of one another to fill each compartment 149 of the carton 148. The carton 148 can have an area of 625 square centimeters to 2500 square centimeters. The carton 148 can have a length and width of 25 to 50 cm. The carton 148 can have an area four times that of the projected area of the pouch 102. The carton 148 can have a length and width twice that of the pouch 102. The ratio of the length of the medical fluid chamber 104 of the blood line set 100 to the length and/or width of the compartment 149 can be greater than 0.7.

Each compartment 149 of the carton 148 can have an area that fits the pouch 102. The area of the compartment 149 can be slightly smaller than the pouch 102, which is typically formed of a flexible material that can bend against walls of the compartment 149. For example, each compartment 149 can have a length and/or width of 15 to 25 cm. The projected area of each compartment can be 150 to 625 square centimeters.

Figure 9:
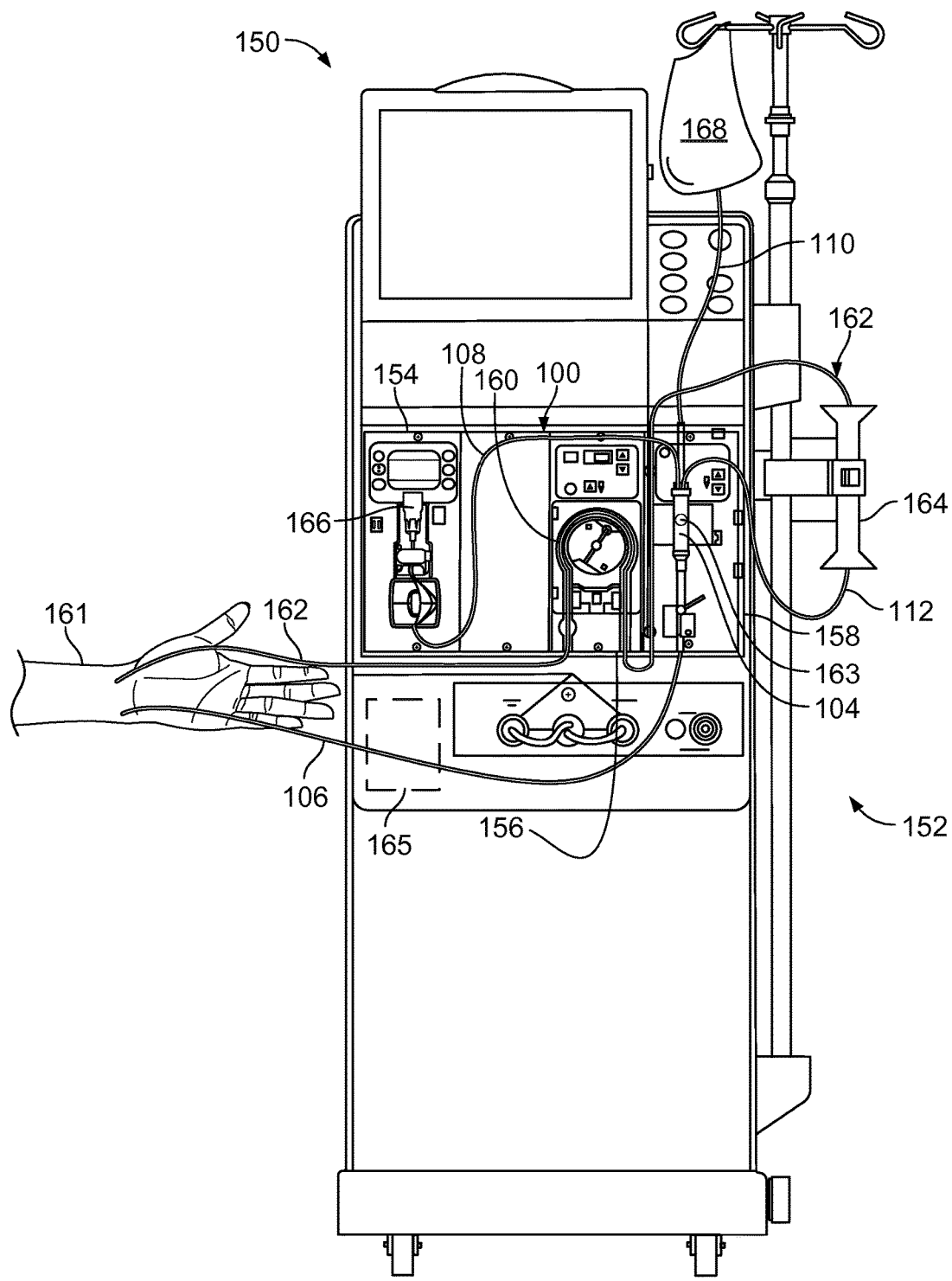
FIG. 9 is a hemodialysis system including a blood line set.
Figure 10:
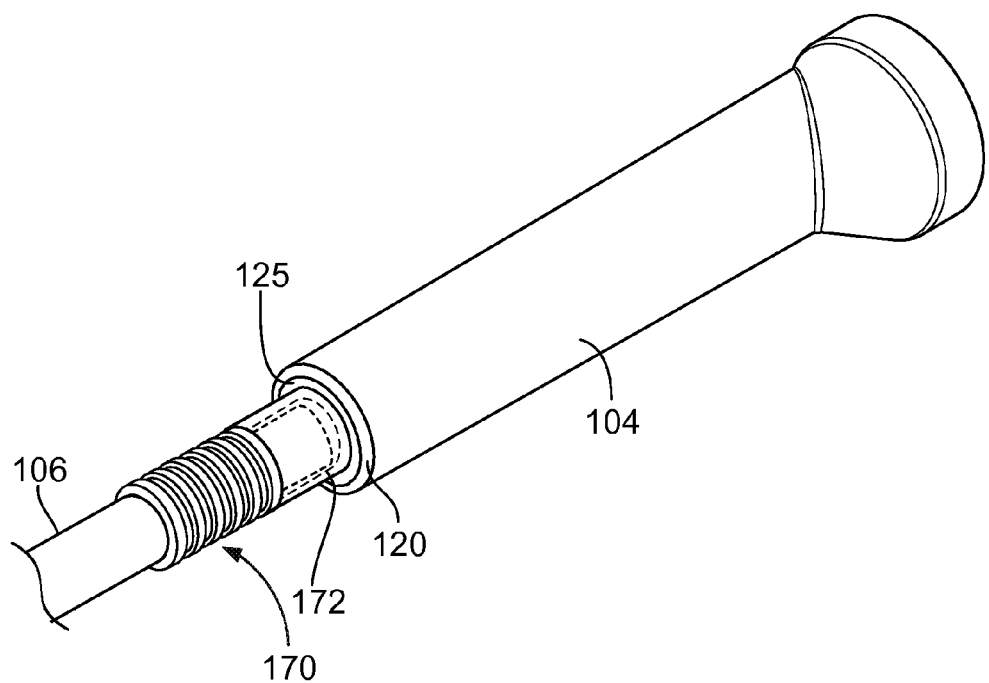
FIG. 10 is a perspective view of a medical fluid chamber with another example of a cuff attached to a bottom portion of the medical fluid chamber.
Figure 11:
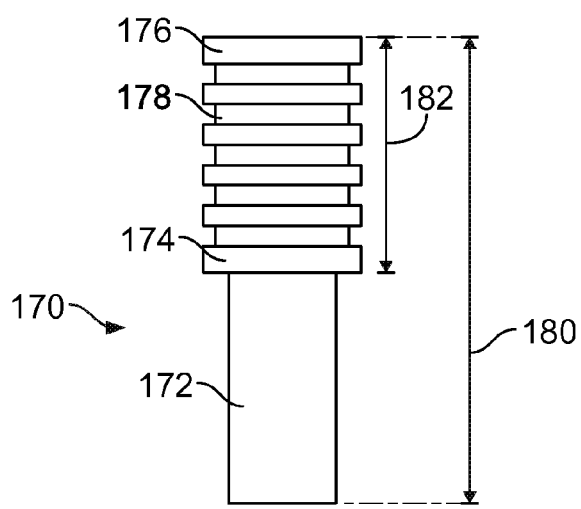
FIG. 11 is a front view of the cuff attached to the bottom portion of the medical fluid chamber of FIG. 10.

The blood line set 100 can be used as part of a hemodialysis system to treat a patient with renal dysfunction. Referring to FIG. 9, a hemodialysis system 150 includes a hemodialysis machine 152 having a drug delivery module 154, a blood pump module 156, and a level detector module 158. A blood pump 160 disposed on the blood pump module 156 draws blood from a patient 161 and pumps the blood through a patient line 162 attached to the blood pump module 156. The medical fluid chamber 104 of the blood line set 100 is installed on the level detector module 158, which includes a level detector 163 to detect a level of fluid in the medical fluid chamber 104. Blood travels through a dialyzer 164, which filters the blood and removes waste products from the blood. The blood travels alongside a dialysate solution prepared by a dialysate preparation system 165 housed in the hemodialysis machine 152. The dialysate solution can include salt (e.g., sodium bicarbonate), a buffer (e.g., sodium acetate), and purified water (e.g., reverse osmosis water). Wastes from the blood diffuse into the dialysate solution through a filter, a filtering membrane, filtering microtubules, or some other filtering feature of the dialyzer 164 that separates the blood and the dialysate solution.

After the dialyzer 164 filters the blood, the filtered blood exits the dialyzer 164 into the blood line set 100 through the inlet fluid line 112. The inlet fluid line 108 can serve as a drug line to deliver drugs to the patient 161 during hemodialysis treatment from a drug vial 166 disposed on the drug delivery module 154. The drugs flow from the drug vial 166 through the inlet fluid line 108 into the medical fluid chamber 104. The inlet fluid line 110 can deliver saline from a saline bag 168 to the medical fluid chamber 104. In the medical fluid chamber 104, the saline, drug, and filtered blood mix. The medical fluid chamber 104 slows the flow of the mixture and facilitates release of air entrained in the mixture. The medical fluid chamber 104 thus serves as an air release chamber for the hemodialysis system 150. Furthermore, the filter 119 (shown in FIG. 2) removes particulate matter and debris (e.g., clots) from the mixture as the mixture flows through the outlet fluid line 106 to the patient 161.

Methods of Use

Figure 8:
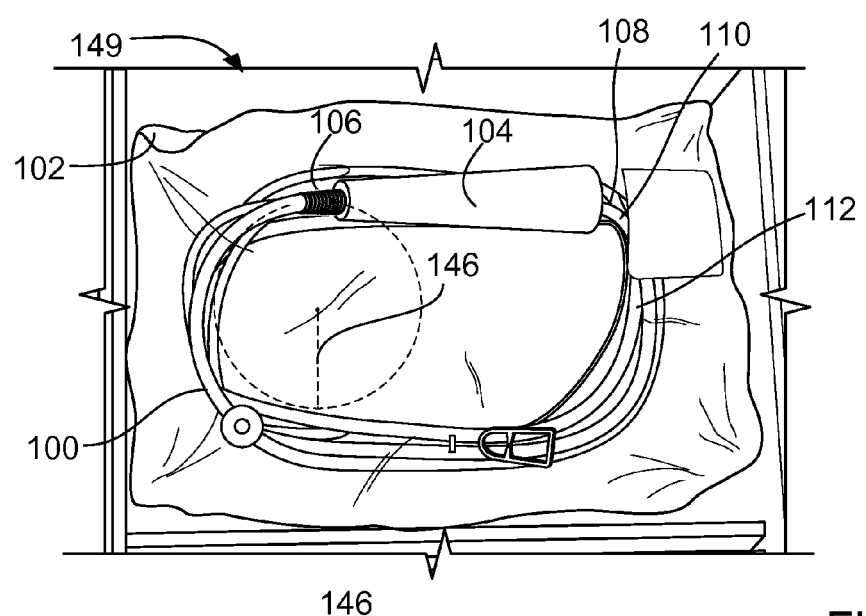
FIG. 8 is a top view of the pouch of FIG. 1.

A method of preparing and using the blood line set 100 for a hemodialysis treatment is described below. Referring to FIGS. 1 and 2, the outlet fluid line 106 and the inlet fluid lines 108, 110, 112 of the blood line set 100 are coiled so that the blood line set 100 can be placed in the pouch 102. Referring to FIG. 8, the outlet fluid line 106 is coiled to have the average radius of curvature 146 within the range as described herein. The outlet fluid line 106 is tightly coiled without causing material damage to the outlet fluid line 106. The inlet fluid lines 108, 110, 112 are coiled to have radii of curvatures substantially equal to or smaller than the average radius of curvature of the outlet fluid line 106 so that the blood line set 100 can fit in the pouch 102 having the dimensions (e.g., length, width, and projected area) as described herein. Similarly, the inlet fluid lines 108, 110, 112 are coiled to have radii of curvatures that do not result in material damage of the inlet fluid lines 108, 110, 112.

Still referring to FIG. 2, the blood line set 100 with coiled fluid lines 106, 108, 110, 112 is placed into the pouch 102. The pouch 102 is then sealed. As shown in FIG. 7, the pouches 102 containing the blood line sets 100 are placed in the compartment 149 of the carton 148. The pouches 102 are arranged and stacked to fill each of the compartments 149. The pouch 102 serves as a compact and sterile packaging container for the blood line set 100, and the carton 148 provides a compact packaging, shipping, and storage container for several pouches 102 containing the blood line set 100. The blood line sets 100 are shipped to the customer (e.g., a dialysis clinic) in this way.

The blood line set 100 can then be used for a treatment process, such as a hemodialysis treatment process described below. Referring to FIG. 8, to carry out such a treatment, an operator typically enters patient parameters and medical treatment information into the hemodialysis machine 152. Before treatment, the operator removes the pouch 102 from the carton 148. The operator removes the blood line set 100 from the pouch 102. The operator connects the inlet fluid line 110 to the saline bag 168 and the inlet fluid line 108 to the drug vial 166. The operator also connects the outlet fluid line 106 of the blood line set 100 to the patient 161 and the inlet fluid line 112 to the dialyzer 164. The operator can bend the outlet fluid line 106 toward the position of the patient 161 without damaging the outlet fluid line 106 as the outlet fluid line 106 exits the medical fluid chamber 104 of the blood line set 100. The operator can bend the outlet fluid line 106 to have the average radius of curvature 146 (shown in FIG. 6) that does not result in material failure of the outlet fluid line 106. The cuff 122 over the outlet fluid line 106 bends with the outlet fluid line 106. As a result, the cuff reduces the likelihood that the operator inadvertently damages the outlet fluid line 106 by bending the outlet fluid line 106 below the average radius of curvature that can kink, yield, or otherwise cause material failure of the walls of the outlet fluid line 106. The dialysate preparation system 165 that prepares dialysate is also fluidly connected to the dialyzer 164.

The operator then initiates the hemodialysis treatment process. During hemodialysis, blood is circulated through the blood circuit (i.e., the various blood lines, the blood line set 100, and the dialyzer 164). At the same time, dialysate is circulated through the dialysate circuit (i.e., various dialysate lines and dialysate components part of the dialysate preparation system 165). Toxins are transferred from the blood to the dialysate, thus ridding the patient's blood of harmful substances. When the hemodialysis treatment is complete, the operator disconnects and disposes the blood fluid line set 100.

Alternative Implementations

The above-described examples pertaining to the blood line set 100 have been described for illustration purposes. Other implementations are understood to be appropriate.

The dimensional and geometric characteristics described for the components of the medical fluid chamber 104, the pouch 102, the cuff 122 and the carton 148 can vary in other implementations. The medical fluid chamber 104 can have a length between, for example, 10 to 15 cm, 15 to 20 cm, and 20 to 25 cm. The length and width of the pouch 102 can be, for example, 15 to 20 cm, 20 to 25 cm, and 25 to 30 cm so that the blood line set 100 with the coiled fluid lines 106, 108, 110, 112 fit within the pouch 102. The projected area of the pouch 102 can be, for example, 225 square centimeters to 400 square centimeters, 400 to 625 square centimeters, or 625 to 900 square centimeters. In some cases, the length and width of the pouch 102 can be the sum of the length of medical fluid chamber 104 and twice the average radius of curvature 146 of the outlet fluid line 106 when the outlet fluid line 106 is coiled. The ratio of the length of the medical fluid chamber 104 to the length and/or width of the pouch 102 can be greater than, for example, 0.5, 0.7, or 0.9.

The outlet fluid line 106 can have an inner diameter 134 between, for example, 2 mm and 6 mm, 6 mm and 10 mm, or 10 mm and 14 mm, and an outer diameter 136 between, for example, 6 mm and 10 mm, 10 mm and 14 mm, or 14 mm and 18 mm. The outlet fluid line 106 can have a wall thickness between, for example, 0.5 mm and 1.5 mm, 1.5 mm and 3 mm, or 3 mm and 4.5 mm. The medical fluid chamber 104 can have a wall thickness between, for example, 1 mm and 2.5 mm, 2.5 mm and 4 mm, or 4 mm and 5.5 mm.

At the protruding sections 128 of the cuff 122, the cuff 122 can have a wall thickness of, for example, 1 mm to 2.5 mm, 2.5 mm to 4 mm, or 4 mm to 5.5 mm. At the recessed sections 130 of the cuff 122, the cuff 122 can have a wall thickness of, for example, 0.5 mm to 1.5 mm, 1.5 mm to 3 mm, or 3 mm to 4.5 mm. The protruding sections 128 can be spaced apart by, for example, 0.5 mm to 1 mm, 1 mm to 1.5 mm, or 1.5 mm to 2 mm. The recessed sections 128 can be spaced by, for example, 0.5 mm to 1 mm, 1 mm to 1.5 mm, or 1.5 mm to 2 mm. Together, the cuff 122 and the outlet fluid line 106 can have a combined minimum wall thickness (e.g., at the recessed sections 130) of, for example, 1 mm to 3 mm, 3 mm to 5 mm, or 5 mm to 7 mm and a combined maximum thickness (e.g., at the protruding sections 128) of, for example, 1.5 mm to 4 mm, 4 mm to 6.5 mm, or 6.5 mm to 8 mm. Additionally, the taper of the cuff 122 can cause the outer diameters and wall thicknesses of the protruding sections 128 and the recessed sections 130 to decrease as the cuff 122 extends in the downward direction. The cuff 122 can have the total length 142 of, for example, 1 cm to 3 cm, 3 cm to 5 cm, or 5 cm to 7 cm. The length 144 can extend beyond the tubular fitting 120 by, for example, 0.5 cm to 1.5 cm, 1.5 cm to 3 cm, or 3 cm to 4.5 cm.

The deformation characteristics of the cuff 122 and the outlet fluid line 106 may vary as well. With the cuff 122, the minimum average radius of curvature 146 without causing material deformation of the outlet fluid line 106 can be, for example, 7 to 10 cm, 10 cm to 13 cm, or 13 cm to 16 cm. The minimum average radius of curvature 146 can be less than, for example, 17 cm, 14 cm, 11 cm, or 8 cm. When the medical fluid tubing is coiled, a ratio of the average radius of curvature 146 to the length of the medical fluid chamber 104 can be between, for example, 0.1 to 0.3, 0.1 to 0.5, 0.1 to 0.7, 0.3 to 0.5, or 0.7 to 0.9.

The carton 148 can have an area of, for example, 625 square centimeters to 1600 square centimeters, 1225 to 2500 square centimeters, or 2025 to 3600 square centimeters. The carton 148 can have a length and width of, for example, 25 to 40 cm, 35 to 50 cm, or 45 to 60 cm. Each compartment 149 of the carton 148 can have a length and/or width of, for example, 12.5 to 20 cm, 17.5 cm to 25 cm, or 22.5 cm to 30 cm. The projected area of each compartment can be, for example, 150 to 400 square centimeters, 300 to 625 square centimeters, or 500 to 900 square centimeters. In some cases, the carton 148 can have between 1 times and 3 times, 3 times and 5 times, or 5 times and 8 times the projected area of the pouch 102. In some cases, the length and width of the carton 148 is between 1 and 2 times, 2 times and 3 times, or 3 times and 4 times the length and width of the pouch 102. The ratio of the length of the medical fluid chamber 104 to the length and/or width of the compartment 149 can be greater than, for example, 0.5, 0.7, or 0.9.

While the outlet fluid line 106 has been described to have a greater inner diameter than the inlet fluid lines 108, 110, 112 to achieve the equalized flow rates, in some implementations, the cross-sectional area of the outlet fluid line 106 can be approximately a sum of the cross-sectional area of the inlet fluid lines 108, 110, 112 so that the flows are approximately equal.

While the inner diameter of the opening 124 of the cuff 122 has been described to be approximately equal to the outer diameter of the tubular fitting 120, in some cases, the inner diameter of the opening 124 can be less than an outer diameter of the tubular fitting 120 such that the cuff 122 fits tightly over the tubular fitting 120. For example, the inner diameter of the cuff 122 can be less than the outer diameter 136 of the outlet fluid line 106 by 0.5 mm to 1 mm, 1 mm to 1.5 mm, or 1.5 mm to 2 mm. The inner diameter of the cuff 122 can be substantially uniform along a length of the cuff 122.

While the pouch 102 has been described as the container for the coiled blood line set 100, in some implementations, the container can be a semi-rigid box (e.g., a cardboard box) that can fit the coiled blood line set. In some cases, the coiled blood line set 100 is placed into a pouch, and the pouch is placed into a container that fits a single pouch.

The cuff 122 has been described to be overmolded or insert molded with the medical fluid chamber 104. In some cases, the cuff 122 can be a separately molded component that slides over the outlet fluid line 106 of the blood line set 100 and engages with the medical fluid chamber 104. The cuff 122 can be bonded to the outlet fluid line 106 and to the medical fluid chamber 104 using an adhesive. In other cases, a cuff 170 includes an insert fitting 172 and a bending portion 174. An outer surface of the insert fitting 172 engages with an inner surface of the tubular fitting 120 such that the insert fitting 172 of the cuff 170 attaches the cuff 170 to the medical fluid chamber 104 when placed into the tubular fitting 120. The bending portion 174 bends with the outlet fluid line 106 and thus serves a similar purpose as the cuff 122. The bending portion 174 includes discontiguous protruding portions 176 and recessed portions 178 having similar geometric characteristics as those described with respect to the protruding portions 128 and the recessed portions 130 of the cuff 122. A total length 180 of the cuff 170 is similar to the total length 142 of the cuff 122. The cuff 170 extends beyond the tubular fitting 120 by a length 182 similar to the length 144 described with respect to the cuff 122. The cuff 170 has similar material characteristics as described with respect to the cuff 122. The cuff 170 can also be adhered or bonded to the insert fitting 172 and to the outlet fluid line 106.

The material characteristics of the cuff 122, the medical fluid chamber 104, and the fluid lines 106, 108, 110, 112 can vary as well. As described herein, the material of the cuff 122 can be elastomeric and can have an elastic modulus between, for example, 0.1 MPa to 1 MPa, 1 MPa to 10 MPa, or 10 MPa to 100 MPa; the material of the outlet fluid line 106 can have an elastic modulus between, for example, 0.1 MPa to 1 MPa, 1 MPa to 10 MPa, or 10 MPa to 100 MPa; and the material of the medical fluid chamber 104 can have an elastic modulus between, for example, 100 MPa to 1000 MPa, 1000 MPa to 5000 MPa, or 5000 MPa to 10000 MPa. The medical fluid chamber 104 can have a durometer of, for example, shore 65D to 75D, 75D to 85D, or 80D to 95D. The medical fluid lines 106, 108, 110, 112 can have a durometer of, for example, shore 60 A to 70 A, 70 A to 80 A, or 80 A to 90 A. The cuff 122 can have a durometer of, for example, shore 60 A to 70 A, 70 A to 80 A, or 80 A to 90 A.

While the cuff 122 has been described to have a uniform cross-section throughout its length, in some cases, the cuff 122 is tapered in a downward direction from the bottom surface 125 of the housing 114 toward an end 126 of the tubular fitting 120.

The cuff 122 can support the outlet fluid line 106, which has been described to experience greater stresses than the inlet fluid lines 108, 110, 112. In some examples, a cuff can be sized and dimensioned to support the inlet fluid lines 108, 110, 112. While the cuff 122 has been described to have protruding portions 128 and recessed portions 130, in some implementations, the cuff has a uniform outer diameter throughout.

While the carton 148 has been described to have four compartments 149, in some implementations, the carton can have additional or fewer compartments. For example, the carton can have a single compartment that can fit several pouches side-by-side. The carton can have a five, six, or more compartments, each compartment fitting at least one pouch.

While the fluid line set 100 has been described as a blood line set, in some implementations, the fluid line set 100 can conduct fluids of types other than blood. For example, the fluid line set 100 can be an apheresis line set, an enteral feeding line set, a parenteral feeding line set, or other appropriate medical line set to transport fluids. In some cases, the fluid line set 100 can conduct plasma, water, purified water, salt solutions, buffer solutions, gas, priming solution, medication, or other appropriate fluids.

While a number of examples have been described for illustration purposes, the foregoing description is not intended to limit the scope of the implementations disclosed herein. There are and will be other examples and modifications within the scope of the following claims.

What is claimed is:

1. A tubing set, comprising:
   a rigid medical fluid chamber comprising a housing and a tubular fitting extending from the housing, wherein the rigid medical fluid chamber is an air release chamber having an inlet for blood and an outlet for blood, the tubular fitting corresponding to the outlet;
   a plurality of inlet fluid lines connected to a cap of the rigid medical fluid chamber;
   medical fluid tubing connected to the tubular fitting such that the medical fluid tubing is in fluid communication with the rigid medical fluid chamber; and
   a cuff positioned over a length of the medical fluid tubing to inhibit denting of a wall of a length of the medical fluid tubing when the medical fluid tubing is coiled, the length of the medical fluid tubing being connected to the tubular fitting and extending beyond the tubular fitting.

2. The tubing set of claim 1, wherein the rigid medical fluid chamber has a first rigidity, the medical fluid tubing has a second rigidity less than the first rigidity, and the cuff has a third rigidity greater than the second rigidity and less than the first rigidity.

3. The tubing set of claim 2, wherein the first rigidity comprises a first elastic modulus, the second rigidity comprises a second elastic modulus, and the third rigidity comprises a third elastic modulus, the first elastic modulus being between 500 MPa and 2500 MPa, the second elastic modulus being between 0.5 MPa and 10 MPa, and the third elastic modulus being between 0.5 and 10 MPa.

4. The tubing set of claim 3, wherein the first rigidity comprises a first wall thickness, the second rigidity comprises a second wall thickness, and the third rigidity comprises a third wall thickness, the first wall thickness being between 2 and 5 mm, the second wall thickness being between 1 mm and 3 mm, and the third wall thickness being between 2 mm and 4 mm.

5. The tubing set of claim 1, wherein the rigid medical fluid chamber has a length between 13 cm and 16 cm.

6. The tubing set of claim 1, wherein, when the medical fluid tubing is coiled, the medical fluid tubing is defined by a radius of curvature, and a ratio of the radius of curvature to a length of the rigid medical fluid chamber is between 0.3 and 0.7.

7. The tubing set of claim 1, wherein when the medical fluid tubing is coiled, a radius of curvature of the medical fluid tubing is less than 18 cm.

8. The tubing set of claim 1, wherein a radius of curvature is defined by a radius of a 180-degree arc that circumscribes the medical fluid tubing, the arc comprising a first end and a second end defining a diameter of the arc, the first end located along a free end of the cuff.

9. The tubing set of claim 1, wherein the cuff comprises a plurality of first sections having a first outer diameter and a plurality of second sections having a second outer diameter that is less than the first outer diameter, the plurality of first and second sections forming a plurality of discontiguous slots.

10. The tubing set of claim 9, wherein an inner diameter of the cuff is substantially uniform along a length of the cuff.

11. The tubing set of claim 1, wherein an inner surface of the cuff is in contact with an outer surface of the medical fluid tubing and an outer surface of the tubular fitting.

12. The tubing set of claim 1, wherein an outer surface of the cuff is in contact with an inner surface of the tubular fitting.

13. The tubing set of claim 1, wherein the cuff is overmolded to the tubular fitting extending from the rigid medical fluid chamber.

14. The tubing set of claim 1, wherein the cuff is bonded to the tubular fitting extending from the rigid medical fluid chamber.

15. The tubing set of claim 1, further comprising a filter disposed above the tubular fitting in the rigid medical fluid chamber such that fluid exiting the rigid medical fluid chamber passes through the filter.

16. A package of medical fluid tubing sets, comprising:
a compartment having a compartment length; and
at least one medical fluid tubing set, the at least one medical fluid tubing set comprising:
a rigid medical fluid chamber having a chamber length, the rigid medical fluid chamber comprising a housing and a tubular fitting extending from the housing, wherein the rigid medical fluid chamber is an air release chamber having an inlet for blood and an outlet for blood, the tubular fitting corresponding to the outlet;
a plurality of inlet fluid lines connected to a cap of the rigid medical fluid chamber;
medical fluid tubing connected to the tubular fitting such that the medical fluid tubing is in fluid communication with the rigid medical fluid chamber; and
a cuff positioned over a length of the medical fluid tubing to inhibit denting of a wall of a length of the medical fluid tubing when the medical fluid tubing is coiled, the length of the medical fluid tubing being connected to the tubular fitting and extending beyond the tubular fitting;
wherein a ratio of the chamber length to the compartment length is greater than 0.7.

17. The package of claim 16, wherein the rigid medical fluid chamber has a length between 13 cm and 16 cm.

18. The package of claim 16, wherein the medical fluid tubing is coiled and defined by a radius of curvature, and a ratio of the radius of curvature to a length of the rigid medical fluid chamber is between 0.3 and 0.7.

19. The package of claim 16, wherein a radius of curvature of the medical fluid tubing is less than 18 cm.

20. The package of claim 16, wherein a radius of curvature is defined by a radius of a 180: degree arc that circumscribes the medical fluid tubing, the arc comprising a first end and a second end defining a diameter of the arc, the first end located along a free end of the cuff.

21. The package of claim 16, wherein the medical fluid tubing set further comprises a filter disposed above the tubular fitting in the rigid medical fluid chamber such that fluid exiting the rigid medical fluid chamber passes through the filter.

22. A tubing set, comprising:
a rigid medical fluid chamber comprising a housing and a tubular fitting extending from the housing, wherein the rigid medical fluid chamber is an air release chamber having an inlet for blood and an outlet for blood, the tubular fitting corresponding to the outlet;
medical fluid tubing connected to the tubular fitting such that the medical fluid tubing is in fluid communication with the rigid medical fluid chamber;
a filter disposed above the tubular fitting in the rigid medical fluid chamber such that fluid exiting the rigid medical fluid chamber passes through the filter; and
a cuff positioned over a length of the medical fluid tubing to inhibit denting of a wall of a length of the medical fluid tubing when the medical fluid tubing is coiled, the length of the medical fluid tubing being connected to the tubular fitting and extending beyond the tubular fitting.

23. The tubing set of claim 22, wherein:
the rigid medical fluid chamber has a first rigidity, the medical fluid tubing has a second rigidity less than the first rigidity, and the cuff has a third rigidity greater than the second rigidity and less than the first rigidity, and
the first rigidity comprises a first elastic modulus, the second rigidity comprises a second elastic modulus, and the third rigidity comprises a third elastic modulus, the first elastic modulus being between 500 MPa and 2500 MPa, the second elastic modulus being between 0.5 MPa and 10 MPa, and the third elastic modulus being between 0.5 and 10 MPa.

24. The tubing set of claim 22, wherein the rigid medical fluid chamber has a length between 13 cm and 16 cm.

25. The tubing set of claim 22, wherein the cuff comprises a plurality of first sections having a first outer diameter and a plurality of second sections having a second outer diameter that is less than the first outer diameter, the plurality of first and second sections forming a plurality of discontiguous slots.

26. The tubing set of claim 22, wherein an outer surface of the cuff is in contact with an inner surface of the tubular fitting.

27. A package of medical fluid tubing sets, comprising:
a compartment having a compartment length; and
at least one medical fluid tubing set, the medical fluid tubing set comprising:
a rigid medical fluid chamber having a chamber length, the rigid medical fluid chamber comprising a housing and a tubular fitting extending from the housing, wherein the rigid medical fluid chamber is an air release chamber having an inlet for blood and an outlet for blood, the tubular fitting corresponding to the outlet;
medical fluid tubing connected to the tubular fitting such that the medical fluid tubing is in fluid communication with the rigid medical fluid chamber;
a filter disposed above the tubular fitting in the rigid medical fluid chamber such that fluid exiting the rigid medical fluid chamber passes through the filter; and
a cuff positioned over a length of the medical fluid tubing to inhibit denting of a wall of a length of the medical fluid tubing when the medical fluid tubing is coiled, the length of the medical fluid tubing being connected to the tubular fitting and extending beyond the tubular fitting;
wherein a ratio of the chamber length to the compartment length is greater than 0.7.

28. The package of claim 27, wherein the rigid medical fluid chamber has a length between 13 cm and 16 cm.

29. The package of claim 27, wherein the medical fluid tubing is coiled and defined by a radius of curvature, and a ratio of the radius of curvature to a length of the rigid medical fluid chamber is between 0.3 and 0.7.

30. The package of claim 27, wherein a radius of curvature of the medical fluid tubing is less than 18 cm.

31. The package of claim 27, wherein a radius of curvature is defined by a radius of a 180-degree arc that circumscribes the medical fluid tubing, the arc comprising a first end and a second end defining a diameter of the arc, the first end located along a free end of the cuff.

* * * * *

UNITED STATES PATENT AND TRADEMARK OFFICE
CERTIFICATE OF CORRECTION

PATENT NO. : 10,195,411 B2
APPLICATION NO. : 14/801622
DATED : February 5, 2019
INVENTOR(S) : Christopher Yim Chau and Irving Hernandez Page 1 of 1

It is certified that error appears in the above-identified patent and that said Letters Patent is hereby corrected as shown below:

In the Claims

Claim 20
Column 15, Line 53, delete "180: degree" and insert --180-degree--.

Signed and Sealed this
Second Day of April, 2019

Andrei Iancu
*Director of the United States Patent and Trademark Office*